United States Patent
Young et al.

(10) Patent No.: US 8,082,027 B2
(45) Date of Patent: Dec. 20, 2011

(54) PORTABLE USB ELECTROCARDIOGRAPH SYSTEM AND METHOD

(75) Inventors: Brian J. Young, Germantown, WI (US); James R. Peterson, Fond du Lac, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 12/775,966

(22) Filed: May 7, 2010

(65) Prior Publication Data

US 2011/0275948 A1 Nov. 10, 2011

(51) Int. Cl.
*A61B 5/04* (2006.01)

(52) U.S. Cl. ..................................... 600/509

(58) Field of Classification Search ............... 717/178; 715/736; 714/33; 320/106; 607/4; 600/509
See application file for complete search history.

(56) References Cited

U.S. PATENT DOCUMENTS

| | | | |
|---|---|---|---|
| 4,625,730 A * | 12/1986 | Fountain et al. | ............ 607/4 |
| 5,456,261 A | 10/1995 | Luczyk | |
| 5,792,065 A | 8/1998 | Xue et al. | |
| 5,876,351 A | 3/1999 | Rohde | |
| 6,282,440 B1 | 8/2001 | Brodnick et al. | |
| 6,304,772 B1 | 10/2001 | Taha et al. | |
| 6,351,664 B1 | 2/2002 | Brodnick | |
| 6,507,753 B1 | 1/2003 | Taha et al. | |
| 6,564,090 B2 | 5/2003 | Taha et al. | |
| 6,597,943 B2 | 7/2003 | Taha et al. | |
| 6,810,282 B2 | 10/2004 | Taha et al. | |
| 7,076,287 B2 | 7/2006 | Rowlandson | |
| 7,328,061 B2 | 2/2008 | Rowlandson | |
| 7,509,159 B2 | 3/2009 | Xue et al. | |
| 2006/0248398 A1* | 11/2006 | Neel et al. | ............ 714/33 |
| 2008/0042616 A1* | 2/2008 | Monks et al. | ............ 320/106 |

* cited by examiner

*Primary Examiner* — George Manuel
*Assistant Examiner* — Robert Wieland
(74) *Attorney, Agent, or Firm* — Andrus, Sceales, Starke & Sawall, LLP

(57) ABSTRACT

The system and method of the present application includes an ECG acquisition device having a USB connector for connecting the device to a host device and a patient connector for connecting the device to a patient with ECG leads. The ECG acquisition device of the present system further includes a processor and storage medium, a power management and brokering module, a USB communications control module, an ECG acquisition circuit, and a patient isolation module. Unlike prior art ECG acquisition systems, the system of the present application affords a truly portable ECG acquisition device that may be connected through the USB connector to any host device having software processing capabilities and a display. The ECG acquisition device auto-loads and runs ECG monitoring software onto the host device eliminating the need to install additional acquisition software and/or drivers to the host device, and allows the acquisition device to interface with a host device of varying platforms.

23 Claims, 4 Drawing Sheets

PORTABLE USB ELECTROCARDIOGRAPH SYSTEM AND METHOD

FIELD

The present application is directed to the field of patient monitoring and diagnostic electrocardiography systems. More specifically, the present application is directed to the field of portable ECG systems.

BACKGROUND

In current electrocardiograph (ECG) systems, there exists solutions whereby a set of ECG leads are configured for collecting ECG data from a patient and delivering that signal from the collected ECG data to a monitor or computing device. In current systems, the computing device must have software pre-installed for receiving, compiling and providing a user interface for use with the ECG system.

Further, current monitoring systems may also require the user to install special device drivers or other residual changes to the host computing device in order to utilize the ECG system. These requirements make it difficult to implement a fully portable ECG system, whereby a user such as a physician or other clinical worker may use the ECG leads with any available computing device. Obviously, the current ECG systems make it very difficult to have a true portable ECG system as computing devices must be equipped with special software and/or devices, but the current systems also make portable ECG collection and analysis expensive by requiring multiple licenses and/or installation on a number of computing devices in a healthcare environment.

An embodiment of an ECG system 10 of the prior art is illustrated in FIG. 1. This system 10 includes an acquisition device 20, having a USB communication control module 30, an ECG analog to digital converter 35 and a patient isolation module 40. This prior art solution also includes a patient connector 70 (ECG leads), connecting the acquisition device 20 to the patient 80. The acquisition device 20 further includes a USB connector 60 for coupling to a monitoring device 50. Again, it should be noted that this acquisition device includes only a patient isolation module 40, which is required in electronic devices that are attached to patients, a USB communication control 30 that acts as an interface between the acquisition device 20 and the monitoring device 50, and the converter 35 that prepares the acquired signal for the software application resident on the monitoring device 50. In essence, software on the monitoring device 50, through the USB connector 60, controls the entire operation of the acquisition system 10. The acquisition device 20 in this case is not entirely a portable acquisition device or complete ECG system at all, but rather a mere middleman or transfer device between the monitoring device 50, and the patient connector 70. As stated previously, this system 10 is severely limited in that it can only operate with monitoring devices 50 that have the appropriate resident software or drivers. Further, such systems do not include an acquisition device 20 equipped with power management and brokering for use with host devices with limited capabilities for providing start-up power.

SUMMARY

The system and method of the present application includes an ECG acquisition device having a USB connector for connecting the device to a host device and a patient connector for connecting the device to a patient with ECG leads. The ECG acquisition device of the present system further includes a processor and storage medium, a power management and brokering module, a USB communications control module, an ECG acquisition circuit, and a patient isolation module. Unlike prior art ECG acquisition devices, the system of the present application affords a truly portable ECG acquisition system that may be connected through the USB connector to any host device having software processing capabilities and a display. The ECG acquisition device auto-loads and runs ECG monitoring software onto the host device eliminating the need to install additional acquisition software and/or drivers to the host device, and allows the acquisition device to interface with a host device of varying platforms.

A portable electrocardiograph (ECG) acquisition system, the system comprising an acquisition device, the acquisition device including a storage medium including a set of executable code embodying a host software application in a plurality of formats, an ECG connector including a set of ECG leads, wherein the ECG leads collect a set of ECG data from a patient, a USB connector, wherein the USB connector is configured to couple the acquisition device with a host device, an ECG acquisition subsystem module, wherein the ECG acquisition module controls the collection of the set of ECG data from the patient, and processor, wherein the processor loads the set of executable code in an appropriate one of the plurality of formats on to the host device and executes the set of executable code in the host device when the USB connector is coupled with the host device, and further wherein the executed code starts the software application and displays the software application on a display of the host device.

An electrocardiograph (ECG) acquisition device, the device comprising a storage medium including a set of executable code embodying a host software application in a plurality of formats, an ECG connector for connecting a set of ECG leads, wherein the ECG leads collect a set of ECG data from a patient, a USB connector, wherein the USB connector is configured to couple the acquisition device with a host device, an ECG acquisition subsystem module, wherein the ECG acquisition subsystem module controls the collection of the set of ECG data from the patient, and a processor, wherein the processor communicates with the host device to identify an appropriate one of the platforms of the host device and loads the set of executable code on to the host device and executes the set of executable code in the host device when the USB connector is coupled with the host device, and further wherein the executed code starts the software application and displays the software application on a display of the host device.

A method of portable collection of an electrocardiograph (ECG) from a patient with a portable USB ECG acquisition device, the method comprising connecting the acquisition device to a host device with a USB connector, identifying the platform of the host device with a processor in the acquisition device, automatically loading a set of executable code from a storage medium in the acquisition device having an appropriate format for the host device on to the host device, automatically executing the set of executable code on the host device with the processor, starting an ECG monitoring software application, connecting a set of ECG leads to the patient, wherein the ECG leads are coupled with the acquisition device, and receiving in the acquisition device commands from a user operating the software application on the host device, wherein the commands initiate collecting a set of ECG data from the patient.

DETAILED DESCRIPTION

Figure 1:
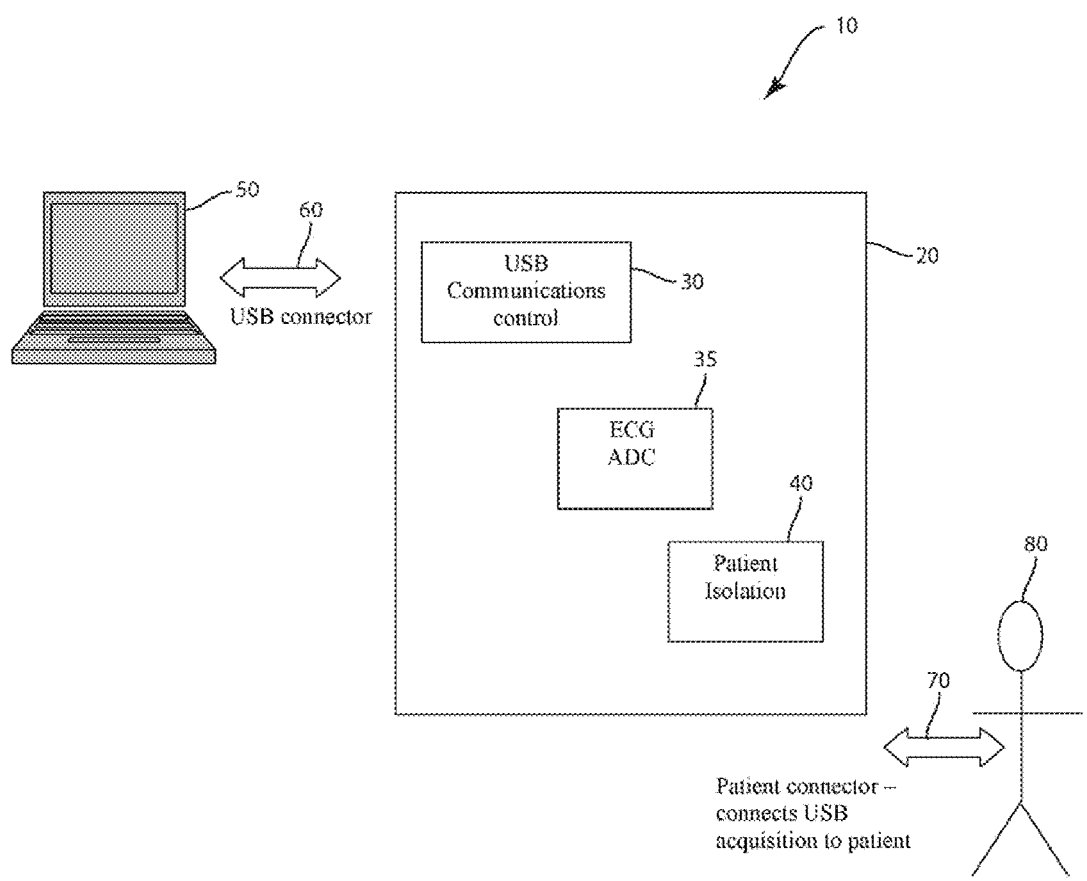
FIG. 1 is a schematic block diagram illustrating an embodiment of a portable USB electrocardiograph system of the prior art.
Figure 2:
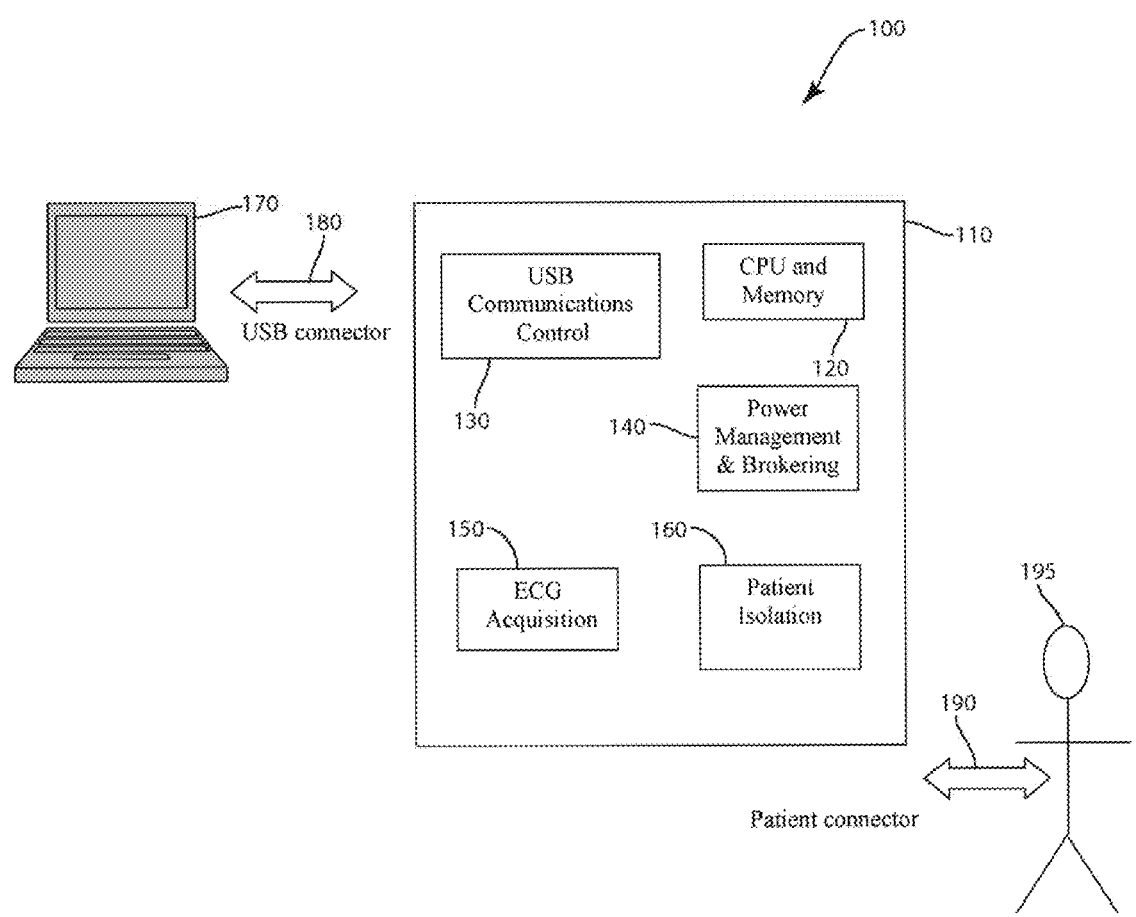
FIG. 2 is a schematic block diagram illustrating an embodiment of a portable USB electrocardiograph system of the present application.

An embodiment of the acquisition system 100 of the present application is depicted in FIG. 2. Here, an acquisition device 110 includes a CPU and memory 120, a USB communication control 130, a power management and brokering module 140, an ECG acquisitions module 150 and a patient isolation module 160. The acquisition device 110 is coupled to a patient 195 with a patient connector 190, and further coupled to a host device 170 with a USB connector 180.

Referring still to FIG. 2, the acquisition system 100 includes a patient connector 190 that utilizes ECG leads to connect with the patient 195. The ECG leads may be a standard 12-lead configuration for collecting ECGs, or any other lead configuration known in the art to collect ECG data from the patient 195. The end of the patient connector 190 connects directly to the acquisition device 110 and may be hardwired to the acquisition device 110 or removable. Furthermore, the patient connector 190 may be a continuous cable from the acquisition device 110 to the set of ECG leads, or may alternatively be a cable extending from the data from the acquisition device 110 having an adapter-type end in order to connect with a variety of possible ECG lead configurations. The patient isolation module 160 is an optical or other-known device in the art that isolates the patient 195 from power mains so that the patient 195 is not exposed dangerously to current power sources. Patient isolation modules 160 are known in the art and are a standard of patient-connected medical electronics.

The USB connector 180 preferably protrudes from the acquisition device 110 and is a standard USB-type connector as known in the art. The requirements of the host device 170 of the present acquisition system 100 is to include a USB port, have a processor and storage medium in order to store and execute a set of executable code in the form of a software application. The host device 170 must also include a display and input/output devices so that a user may interact with the software (SW) application. Accordingly, such qualifying host devices 170 include, but are not limited to, a PC, a laptop, a PDA, cell phone, or any other personal computing device. As will be discussed in further detail in this application, the acquisition device 110, and its corresponding software, will be capable of interacting with a host device 170 having a multitude of platforms and/or operating systems. The USB communications control module is a subsystem that controls the serial communications between the acquisition device 110 and the host system 170 via the USB port of the acquisition device 110, and will manage all communications between the acquisition device 110 and the host device 170 such that they are compliant with USB standards for communication.

The CPU and memory 120 includes a storage medium and a processor. The storage medium stores an SW application in the form of a set of executable code in a number of formats to accommodate a host device 170 having any computing platform. The processor effectuates the loading and executing of this code at the appropriate time for the appropriate platform, which will be discussed in further detail below. Lastly, upon receiving instructions from the SW application, the ECG acquisition module 150 will facilitate the collection of ECG data from the patient 195 through the patient connector 190.

The power management and brokering module 140 is a module included in the embodiment of the present system. When the acquisition device 110 is plugged into a host device 170 that is not a device with an adequate power supply, an internal power source with power management and power brokering capabilities may be used so that the acquisition device 110 can be used with mobile host platforms.

Still referring to FIG. 2, in operation when a user plugs the USB connector 180 of the acquisition device 110 into the host device 170, the technical effect is that the processor communicates with the host device 170 to identify the platform of the host device 170, and then the processor effectuates the loading of the appropriate SW application into the host device 170 according to the platform of the host device 170. The processor then executes the SW application on the host device 170. A user then interacts with the SW application in order to monitor a patient and collect ECG data from that patient. The SW application is further configured to organize, review and manipulate the ECG data in a way suitable for the user, which will be discussed further below as well.

In operation, when the acquisition device 110 is plugged into a host device 170, the acquisition device will select the appropriate SW application by platform and the SW application will auto-run from the acquisition device 110, which means that it does not need to be installed on the host device 170. However, if the host device 170 is one that has been used with this acquisition system 100, the software may have been already saved on the host device 170. Following, the SW application is loaded directly from the acquisition device 110 and is executed. The auto-run SW application of the host device 170 platform includes a user interface which allows a user to control and communicate with the ECG acquisition subsystem module 150 on the acquisition device 110, to enter patient and test information for ECG acquisitions, to conduct real-time signal conditioning, e.g., filtering for noise and display of the ECG signal, to perform automated configurized analysis of the signals including analysis for the purposes of indicating signal quality, lead placement problems, ECG measurement/interpretation. The SW application further allows the users to generate a report of the acquired and analyzed ECG data in either a printed report or digital storage format, to review and make basic physician over-read edits to the generated ECG reports, print the report using printing devices available to the host device 170 platform, and to transfer digital records of recorded ECGs back to the acquisition device 110 for storage.

Figure 3:
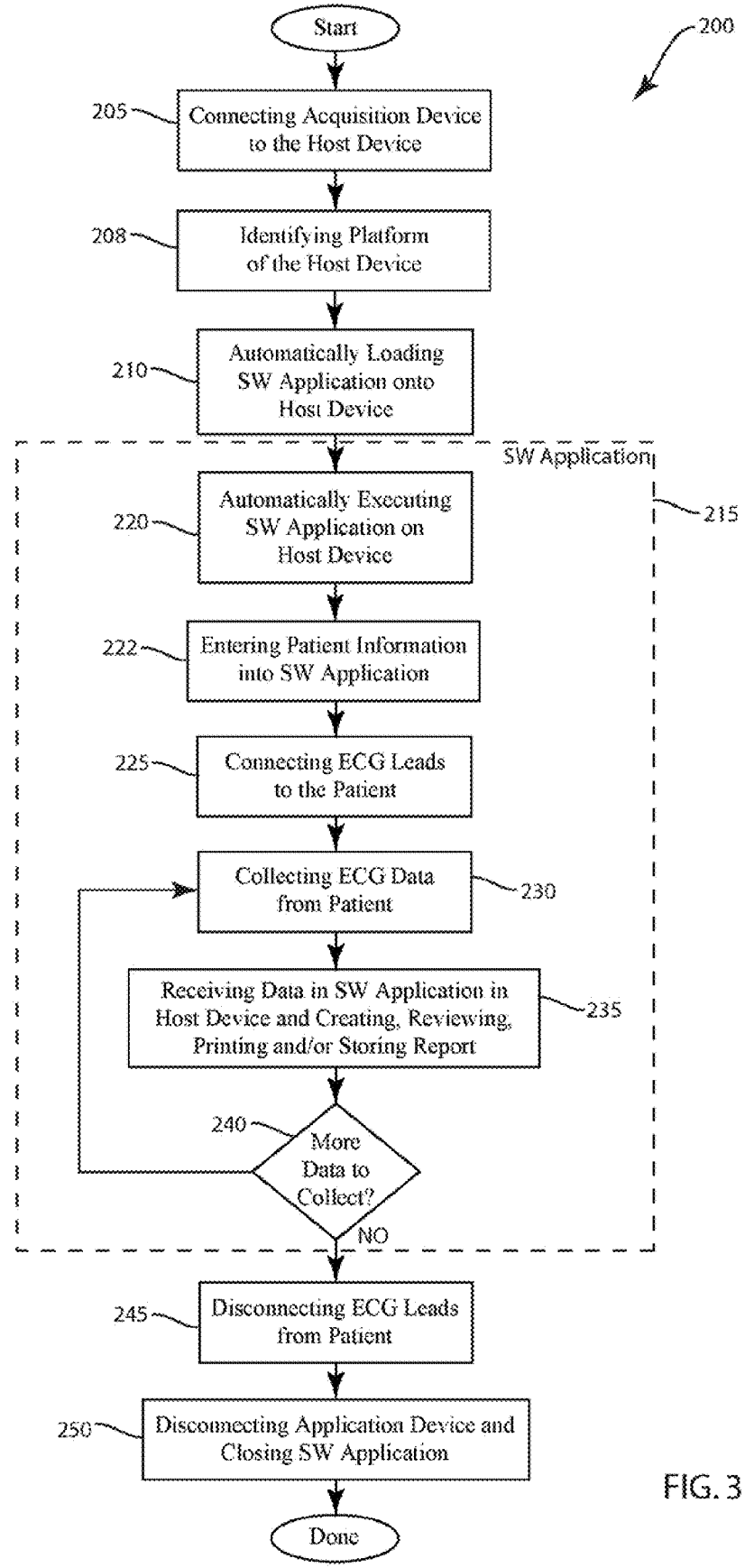
FIG. 3 is a flowchart illustrating an embodiment of a portable USB method of the present application.

An embodiment of the acquisition method 200 of the present application is included in the flowchart of FIG. 3. It should be noted that this flowchart includes both software functions as well as clinical workflow steps, and that the software portions of the acquisition method 200 will be parsed out in the appended claim set. Referring to FIGS. 2 and 3 simultaneously, in step 205 of the acquisition method 200, the acquisition device 110 is connected to the host device 170. In step 208, the processor identifies the platform of the host device 170, and in step 210, the SW application having an appropriate format is automatically loaded to the host device 170. Once the SW application is loaded, the SW application steps 215 include first in step 220, the acquisition device 110 automatically executing the SW application on the host device 170. In step 222, a user may then enter patient information for the patient to be monitored into the SW application. In step 225, the clinician or user connects the ECG leads to the patient. In step 230, upon instructing the system through the SW application, ECG data is collected from the patient, and in step 235, the data is received in the SW application on the host device, where the data may be analyzed, and reports may be created, reviewed, printed and/or stored. In step 240, if there is more data to collect, then the method 200 returns to step 230. If no further data is needed, then in step 245, ECG leads are disconnected from the patient, and in step 250, the acquisition device 110 is disconnected from the host device 170, and the SW application is closed.

Figure 4:
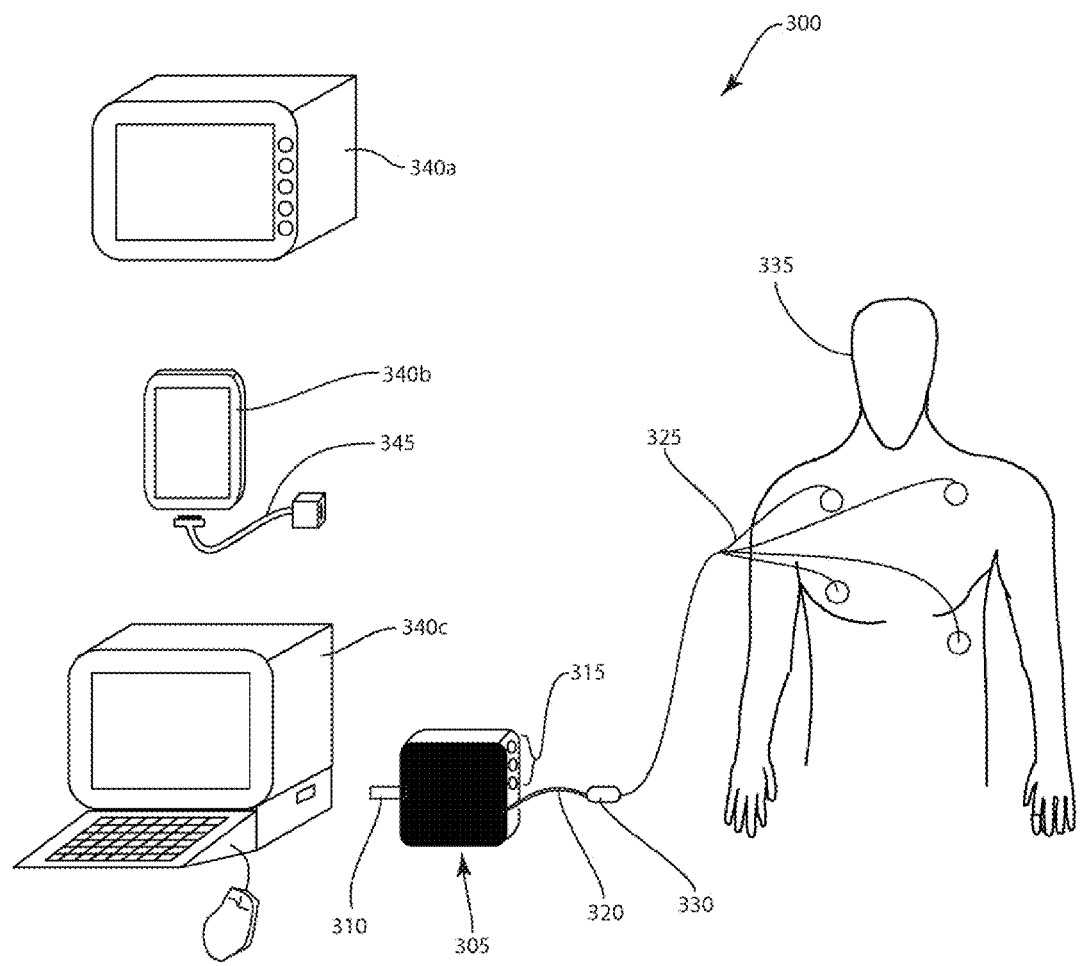
FIG. 4 is a graphical representation illustrating an embodiment of a portable USB system of the present application.

A further embodiment of the present application is illustrated in FIG. 4. Here, the acquisition system 300 again includes an acquisition device 305. The USB connector 310 of the acquisition device 305 is able to connect with any host device 340a, b, c, having a USB port or appropriate adapter 345. A non-exhaustive list of possible examples of host devices 340a, b, c, includes, but is not limited to, a medical monitor 340a including a USB port, a handheld PDA and/or smart phone 340b utilizing an appropriate adapter 345 if no USB port is available, or a laptop or desktop computing device 340c, or any similar computing device.

Still referring to FIG. 4, the acquisition device 305 is further equipped with an LED power/signal indicator 315. This LED power/signal indicator 315 may include any number of LED lights that are utilized to indicate to a user proper application of the acquisition device 305. This LED power/signal indicator 315 may be configurable by the user to indicate whether the appropriate power is available to the acquisition device 305, or whether a signal strength from collected ECG data is adequate for viewing on the SW application on the host device 340a, b, c. Again, this LED power/signal indicator 315 is configurable by the user to detect any number of conditions related to the acquisition device 305. The ECG connector 320, once again is connected to the acquisition device 305 in a removable or fixed manner, and may be a continuous lead to the ECG leads 325, or may include an ECG adapter 330 in order to provide an easier way to disconnect and connect different configurations of ECG leads 325. Here, the patient 335 has four ECG leads 325 attached to its torso. This is an exemplary figure only, and in fact, a standard ECG lead 325 set would include a 12-lead configuration, and in some cases an 8-lead configuration. It is important to note that the system and method of the present application would utilize the various standard ECG lead 325 configurations known in the art, and not necessarily the 4-lead configuration shown in FIG. 4.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A portable electrocardiograph (ECG) acquisition system, the system comprising:
    an acquisition device, the acquisition device including:
        a storage medium including a set of executable code embodying a host software application in a plurality of formats;
        an ECG connector including a set of ECG leads, wherein the ECG leads collect a set of ECG data from a patient;
        a USB connector, wherein the USB connector is configured to couple the acquisition device with a host device;
        an ECG acquisition module, wherein the ECG acquisition module controls the collection of the set of ECG data from the patient; and
        a processor, wherein the processor loads the set of executable code in an appropriate one of the plurality of formats on to the host device and executes the set of executable code in the host device when the USB connector is coupled with the host device, and further wherein the executed code starts the software application and displays the software application on a display of the host device, including displaying the set of collected ECG data on the display of the host device in real time with the software application.

2. The system of claim 1, further comprising a power management module, wherein the power management module manages the power supply of the acquisition device when the host device has a limited power supply for providing start up power.

3. The system of claim 1, further comprising a USB control module, wherein the USB control module electrically controls communications between the host device and the acquisition device.

4. The system of claim 1, further comprising a patient isolation module, wherein the patient isolation module insulates the patient from the acquisition device.

5. The system of claim 1, wherein the software application controls the collection of the set of ECG data from the patient upon a user command through a graphical user interface, and further allows the user to review, manipulate, store and print the set of ECG data.

6. The system of claim 1, wherein the host device is any one of the following devices:
    a desktop personal computer;
    a laptop computer;
    a monitoring device;
    a personal computing device;
    a personal digital assistant; and
    a smart phone.

7. The system of claim 6, further comprising a USB adapter when the host device is not USB compatible.

8. The system of claim 1, further comprising an LED indicator configured in the acquisition device, wherein the LED indicator notifies the user of any combination of power level and ECG signal strength.

9. The system of claim 1, wherein the set of ECG leads are a 12-lead ECG set.

10. The system of claim 1, wherein the ECG connector includes an ECG adapter, thus making the set of ECG leads removably coupled to the ECG connector.

11. An electrocardiograph (ECG) acquisition device, the device comprising:
    a storage medium including a set of executable code embodying a host software application in a plurality of formats;
    an ECG connector for connecting a set of ECG leads, wherein the ECG leads collect a set of ECG data from a patient;
    a USB connector, wherein the USB connector is configured to couple the acquisition device with a host device;
    an ECG acquisition module, wherein the ECG acquisition module controls the collection of the set of ECG data from the patient; and
    a processor, wherein the processor communicates with the host device to identify an appropriate one of the platforms of the host device and loads the set of executable code on to the host device and executes the set of executable code in the host device when the USE connector is coupled with the host device, and further wherein the executed code starts the software application and displays the software application on a display of the host device, including displaying the set of collected ECG data on the display of the host device in real time with the software application.

12. The device of claim 11, further comprising a power management module, wherein the power management module manages the power supply of the acquisition device when the host device has a limited power supply for providing start-up power.

13. The device of claim 11, further comprising a USB control module, wherein the USB control module controls communications between the host device and the acquisition device.

14. The device of claim 11, further comprising a patient isolation module, wherein the patient isolation module electrically insulates the patient from the acquisition device.

15. The device of claim 11, further comprising an LED indicator configured in the acquisition device, wherein the LED indicator notifies the user of any combination of power level and ECG signal strength.

16. The device of claim 11, wherein the set of ECG leads are a 12-lead ECG set.

17. The device of claim 11, wherein the ECG connector includes an ECG adapter, thus making the set of ECG leads removably coupled to the ECG connector.

18. A method of portable collection of an electrocardiograph (ECG) from a patient with a portable USB ECG acquisition device, the method comprising:
   connecting the acquisition device to a host device with a USB connector;
   identifying the platform of the host device with a processor in the acquisition device;
   automatically loading a set of executable code from a storage medium in the acquisition device having an appropriate format for the host device on to the host device;
   automatically executing the set of executable code on the host device with the processor, starting an ECG monitoring software application;
   connecting a set of ECG leads to the patient, wherein the ECG leads are coupled with the acquisition device; and
   receiving in the acquisition device commands from a user operating the software application on the host device, wherein the commands initiate collecting a set of ECG data from the patient, and displaying the set of ECG data on a display of the host: device in real time with the ECG monitoring software application.

19. The method of claim 18, further comprising managing a power supply of the acquisition device when the host device has a limited power supply for providing start up power with a power management module in the acquisition device.

20. The method of claim 18, further comprising electrically insulating the patient from the acquisition device with a patient isolation module in the acquisition module.

21. The method of claim 18, wherein the software application controls the collection of the set of ECG data from the patient upon a user command through a graphical user interface, and further allows the user to review, manipulate, store and print the set of ECG data.

22. The method of claim 18, wherein the host device is any one of the following devices:
   a desktop personal computer;
   a laptop computer;
   a monitoring device;
   a personal computing device;
   a personal digital assistant; and
   a smart phone.

23. The system of claim 18, further comprising notifying the user of any combination of power level and ECG signal strength with an LED indicator configured in the acquisition device.

* * * * *

UNITED STATES PATENT AND TRADEMARK OFFICE
CERTIFICATE OF CORRECTION

| | | |
|---|---|---|
| PATENT NO. | : 8,082,027 B2 | Page 1 of 1 |
| APPLICATION NO. | : 12/775966 | |
| DATED | : December 20, 2011 | |
| INVENTOR(S) | : Young et al. | |

It is certified that error appears in the above-identified patent and that said Letters Patent is hereby corrected as shown below:

In Column 6, Line 67, in Claim 11, delete "USE" and insert -- USB --, therefor.

In Column 8, Line 10, in Claim 18, delete "host: device" and insert -- host device --, therefor.

In Column 8, Line 32, in Claim 23, delete "system" and insert -- method --, therefor.

Signed and Sealed this
Twenty-seventh Day of March, 2012

David J. Kappos
*Director of the United States Patent and Trademark Office*